(12) United States Patent
Savonnet et al.

(10) Patent No.: US 8,940,905 B2
(45) Date of Patent: Jan. 27, 2015

(54) METHOD FOR PREPARING ORGANIC/INORGANIC HYBRID FUNCTIONALIZED SOLIDS HAVING A TRIAZOLE RING

(75) Inventors: Marie Savonnet, Lyons (FR); David Farrusseng, Belmont d'Azegues (FR); Catherine Pinel, Lyons (FR); Delphine Bazer-Bachi, Irigny (FR); Nicolas Bats, Saint Symphorien d'Ozon (FR); Vincent Lecocq, Orlienas (FR)

(73) Assignees: CNRS, Paris Cedex (FR); IFP Energies Nouvelles, Rueil-Malmaison Cedex (FR)

( * ) Notice: Subject to any disclaimer, the term of this patent is extended or adjusted under 35 U.S.C. 154(b) by 446 days.

(21) Appl. No.: 13/503,292

(22) PCT Filed: Oct. 6, 2010

(86) PCT No.: PCT/FR2010/000668
§ 371 (c)(1),
(2), (4) Date: Aug. 2, 2012

(87) PCT Pub. No.: WO2011/048281
PCT Pub. Date: Apr. 28, 2011

(65) Prior Publication Data
US 2012/0296095 A1   Nov. 22, 2012

(30) Foreign Application Priority Data
Oct. 23, 2009 (FR) .................................... 09 05107

(51) Int. Cl.
*C07F 3/06* (2006.01)
*C07F 5/06* (2006.01)
*C07F 3/00* (2006.01)
*C07F 5/00* (2006.01)

(52) U.S. Cl.
CPC .................. *C07F 5/069* (2013.01); *C07F 3/003* (2013.01); *C07F 5/003* (2013.01)
USPC ........................................................ 548/104

(58) Field of Classification Search
USPC .......................................................... 548/104
See application file for complete search history.

(56) References Cited

PUBLICATIONS

Wang et al. "Accessing Postsynthetic Modifcation in a Series of Metal-Organic Frameworks and the Influence of Framework Topology on Reactivity" Inorganic Chemistry, 2009, vol. 48, pp. 296-306.*
Savonnet, M. et al., "Generic Postfunctionalization Route from Amino-Derived Metal-Organic Frameworks," Journal of the American Chemical Society, Apr. 7, 2010, vol. 132, No. 13, pp. 4518-4519; cited in the International Search Report issued in corresponding PCT/FR2010/000668 on Jan. 21, 2011.
Wang, Z. et al., "Accessing Postsynthetic Modification in a Series of Metal-Organic Frameworks and the Influence of Framework Topology on Reactivity," Inorganic Chemistry, 2009, vol. 48, No. 1, pp. 296-306; cited in the International Search Report issued in corresponding PCT/FR2010/000668 on Jan. 21, 2011.
International Search Report issued in corresponding PCT/FR2010/000668 on Jan. 21, 2011.

* cited by examiner

*Primary Examiner* — Joseph Kosack
(74) *Attorney, Agent, or Firm* — Millen, White, Zelano & Branigan, P.C.

(57) ABSTRACT

A process is described for the preparation of a functionalized hybrid solid with an organic-inorganic matrix, crystallized, bearing at least one reactive group based on a triazole ring, from a hybrid solid with an organic-inorganic matrix, MOF—$NH_2$, comprising: i/ introduction, in a polar solvent S1, of said crystallized hybrid solid MOF—$NH_2$, of at least one organic compound Q containing a nitride function $N_3$ and at least one intermediate reagent R containing a nitrite function $NO_2$, ii/ reaction of said reaction mixture, iii/ introduction in the reaction mixture of at least one reagent A bearing an alkyne function or an activated cyanide function, at least one Cu-based catalyst C and at least one polar solvent S2, iv/ reaction of said reaction mixture, v/ filtration and then washing and vi/ drying of said crystallized functionalized hybrid solid.

15 Claims, 1 Drawing Sheet

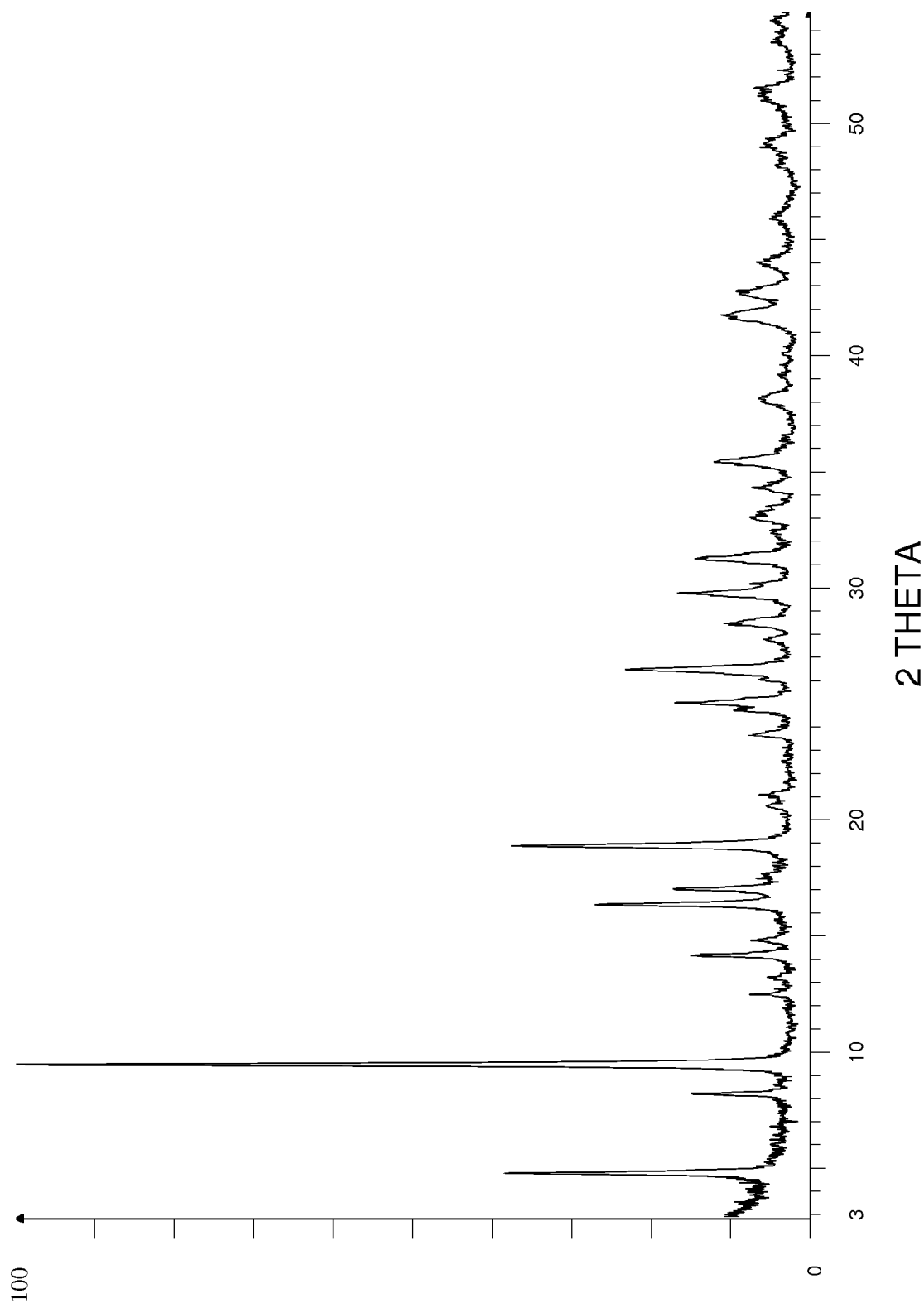

METHOD FOR PREPARING ORGANIC/INORGANIC HYBRID FUNCTIONALIZED SOLIDS HAVING A TRIAZOLE RING

FIELD OF THE INVENTION

The invention relates to the field of functionalization of crystallized hybrid materials with an organic-inorganic matrix for the purpose of obtaining functionalized materials having at least one reactive function, which can for example react selectively when in contact with certain compounds and thus be useful in certain applications. More precisely, the present invention relates to a new process for the preparation of functionalized hybrid materials with an organic-inorganic matrix. These functionalized materials are obtained from crystallized hybrid materials with an organic-inorganic matrix (unfunctionalized) and having an —$NH_2$ function. The unfunctionalized starting materials are called MOF—$NH_2$ hereinafter. The functionalized materials prepared according to the process of the invention have a crystalline structure identical to that of the MOF—$NH_2$ materials from which they are derived by a method of post-synthesis functionalization.

PRIOR ART

The modification of materials by functionalization is a stage that is often necessary in the development of solids possessing the appropriate properties for a given application. Thus, it may be desirable to improve the physicochemical properties of a material, by modifying its surface for example, so that the new properties obtained after modifications are more suitable for applications in separation or catalysis.

One of the means commonly employed for modifying the surface of a material consists of reacting the functional groups initially present on its surface with entities possessing the functions that are required for the application envisaged. The functions present on the surface of a material can be hydroxyl groups (—OH) or any other group (amino-$NH_2$ or —NH— for example) which it is desired to modify in order to orient the chemical reactivity of the surface of the material. The reagents employed will possess the functionalities required for reacting with the groups present initially on the surface of the material, and the result of the reaction will be a new chemical group possessing the desired reactivity. An example of such a conversion consists of reacting the hydroxyl groups of the surface of a silica with a silane bearing an amine function (D. Brunel, *Microporous and Mesoporous Materials*, 1999, 27, 329-344). Thus, the hydroxyl function is converted into an amine function that is more able to catalyse basic reactions or capture $CO_2$ for example. This methodology is applicable to any material initially possessing reactive functions. These materials can be oxides, zeolites or organic/inorganic hybrid materials, also called coordination polymers.

These coordination polymers, the first of which were described in the 1960s, form the subject matter of an increasing number of publications. In fact, the excitement surrounding these materials led to a great variety of structures being achieved in a short time (Férey G., L'actualité chimique, January 2007, No. 304). Conceptually, the porous hybrid solids with mixed organic-inorganic matrix are fairly similar to the porous solids with an inorganic framework. Like the latter, they combine chemical entities, giving rise to porosity. The main difference is in the nature of these entities. This difference is particularly advantageous and forms the basis of the great versatility of this category of hybrid solids. In fact, by using organic ligands, the size of the pores becomes adjustable via the length of the carbon-containing chain of said organic ligands. The framework, which in the case of porous inorganic materials can only accept some elements (Si, Al, Ge, Ga, possibly Zn), can in this case accommodate any cations except the alkali metals. For preparing these hybrid materials, no specific structure-forming agent is required, as the solvent performs this role itself.

It is therefore clear that this family of hybrid materials permits a multiplicity of structures and consequently comprises solids that are finely tuned to the applications for which they are intended.

The coordination polymers comprise at least two elements called linkers and ligands, of which the orientation and the number of binding sites are decisive for the structure of the hybrid material. The different kinds of said ligands and linkers give rise, as already mentioned, to an immense variety of hybrid materials.

By "ligand" is meant the organic part of the hybrid material. Most often these ligands are di- or tri-carboxylates or derivatives of pyridine. Some organic ligands frequently encountered are: bdc=benzene-1,4-dicarboxylate, btc=benzene-1,3,5-tricarboxylate, ndc=naphthalene-2,6-dicarboxylate, bpy=4,4'-bipyridine, hfipbb=4,4'-(hexafluoroisopropylidene)-bisbenzoate, cyclam=1,4,8,11-tetraazacyclotetradecane.

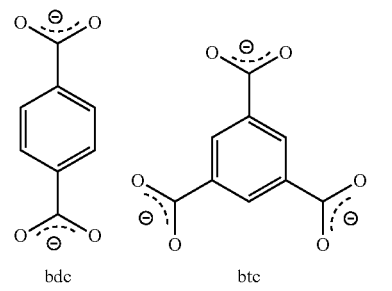

bdc    btc

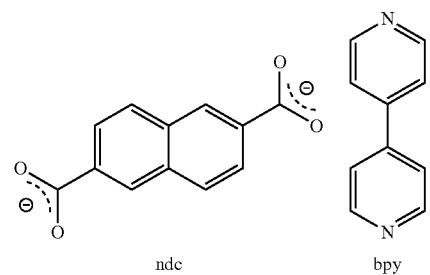

ndc    bpy

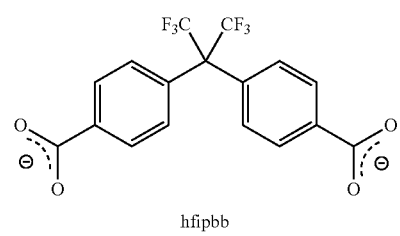

hfipbb

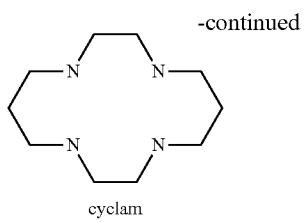
cyclam

By "linker" is meant the inorganic entity of the hybrid material. It may be a single cation, a dimer, trimer or tetramer, or a chain or a plane.

Thus, the teams of Yaghi and Ferey have described a large number of novel hybrid materials (MOF "Metal Organic Framework" series and MIL "Materials of the Lavoisier Institute" series, respectively). Many other teams have followed this route and today the number of new hybrid materials described is expanding rapidly. Most often, research aims to develop ordered structures, with extremely large pore volumes, good thermal stability and adjustable chemical functionalities.

For example, Yaghi et al. describe a series of boron-based structures in patent application US 2006/0154807 and mention their benefits in the field of the storage of gases.

U.S. Pat. No. 7,202,385 discloses an especially complete review of the structures described in the literature and illustrates perfectly the multitude of materials already existing to date.

The preparation of hybrid materials with an organic-inorganic matrix having a reactive organic function (grafted MOF) can be implemented by two main routes: functionalization by self-assembly and post-modification functionalization. Functionalization by self-assembly is carried out by bringing together an organic ligand having the desired reactive function (graft) and an inorganic compound having the role of linker. This method of functionalization is often difficult to implement owing to problems connected with the solubilization and reactivity of the functionalized ligands. In particular, for ligands bearing an —OH, —COOH or —NH$_2$ function there is a risk of interacting with the inorganic compound (linker), leading to solids that are not isostructural with the ungrafted reference MOF. Post-modification functionalization is an interesting alternative method that does not have the limitations of functionalization by self-assembly. Post-modification functionalization consists of directly modifying the organic function of at least one type of ligand present in the MOF by a chemical reaction (grafting), more precisely of substituting the initial organic function with an organic function the reactivity of which is preferred for a subsequent application. This method assumes that the initial MOF has an organic function that is accessible and reactive for grafting. In the literature, organic-inorganic hybrid materials bearing a ligand with an amino function —NH$_2$ such as DMOF-1-NH$_2$ (Z. Q. Wang; K. K. Tanabe, S. M. Cohen, *Inorganic Chemistry*, 2009, 48, 296-306) are described as good substrates for the grafting of numerous functions, in particular aldehydes, isocyanates and acid anhydrides.

The method using post-modification makes it possible to implement methods that are capable of generalization, where the degree of basicity and the hydrophobic/hydrophilic balance can be adjusted by post-functionalization. The objective is therefore to establish a simple method of grafting that can be generalized for numerous groups, such as alkanes, amines, alcohols, thiols, aldehydes, etc., under mild conditions without the release of by-products that may block the pores. The concept of "click chemistry" (H. C. Kolb, M. G. Finn, K. B. Sharpless, Angewandte Chemie, 2001, 40, 2004-2021), introduced in 2001 by K. Barry Sharpless, appears to meet these criteria as it consists of generating synthesis products rapidly and effectively, under mild conditions, by combining small molecular units. This method is described as being effective for the functionalization of a mesoporous silica (A. Schlossbauer, D. Schaffert, J. Kecht, E. Wagner, T. Bein, J. Am. Chem. Soc., 2008, 130 (38), 12558-12559) and of IRMOF-16 (Y. Goto; H. Sato; S. Shinkai, K. Sada, *Journal of the American Chemical Society*, 2008, 130, 14354-14355). In the case of the solid IRMOF-16, the authors use self-assembly to prepare a solid N$_3$—IRMOF-16 and have it react with various alkynes. The drawback of this method is that it requires long stages for synthesis of the organic ligand bearing a nitride function. Moreover, obtaining, by self-assembly from a modified ligand, the corresponding MOF nitride is not obvious (loss of crystallinity, production of unwanted phases, etc.).

The present invention aims to supply a novel process for the preparation of a functionalized solid, the implementation of which makes it possible to overcome the difficulties encountered in the prior art by offering a simple method based on a method of post-modification functionalization. In particular, the novel process of the invention avoids not only the implementation of intermediate stages with recovery of the intermediate compounds but also the need for prior synthesis of a functionalized ligand.

DESCRIPTION OF THE INVENTION

The present invention relates to a process for the preparation of a functionalized hybrid solid with an organic-inorganic matrix, crystallized, bearing at least one reactive group based on a triazole ring, from a crystallized hybrid solid with an organic-inorganic matrix, MOF—NH$_2$, containing an inorganic network of metallic centres joined together at least by organic ligands comprising at least one aromatic ring, at least two carboxylate functions CO$_2^-$ and at least one amine function —NH$_2$, said process comprising at least the following successive stages:

i/ introduction, in a polar solvent S1, of said crystallized hybrid solid MOF—NH$_2$, at least one organic compound Q containing a nitride function N$_3$ and at least one intermediate reagent R containing a nitrite function NO$_2$ in proportions such that the reaction mixture has the following molar composition, based on one molar equivalent of the —NH$_2$ function present in the solid MOF—NH$_2$:

1MOF—NH$_2$:1-150R:1-150Q:100-400S1 ii/ reaction of said reaction mixture at a temperature between 0 and 100° C. for a time between 1 and 24 hours, iii/ introduction, in the reaction mixture, of at least one reagent A comprising at least one alkyne or activated cyanide COCN terminal function, at least one copper-based catalyst C and at least one polar solvent S2 in proportions such that the reaction mixture has the following composition, based on one molar equivalent of the —NH$_2$ function initially present in the solid MOF—NH$_2$:

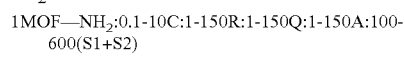
1MOF—NH$_2$:0.1-10C:1-150R:1-150Q:1-150A:100-600(S1+S2)

iv/ reaction of said reaction mixture at a temperature between 0 and 100° C. for a time between 1 and 48 hours, v/ filtration and then washing of said crystallized functionalized hybrid solid, vi/ drying of said crystallized functionalized hybrid solid.

BRIEF DESCRIPTION OF THE DRAWING

FIG. 1 is an x-ray diffraction diagram of a solid according to the invention.

The crystallized hybrid solid with an organic-inorganic matrix prepared according to the process of the invention is a functionalized solid bearing at least one reactive group based on a triazole ring, which is grafted on said organic ligands in place of the —$NH_2$ function present in the solid MOF—$NH_2$ used as starting reactant. The triazole ring is an aromatic heterocycle: the ring is constituted by 5 atoms, namely 3 adjacent nitrogen atoms and 2 adjacent carbon atoms, and has two double bonds, one connecting 2 nitrogen atoms and the other connecting the 2 carbon atoms. More precisely, the reactive group based on said triazole ring is such that said ring is bound to the organic ligand, present in the functionalized solid and derived from an organic ligand present in the solid DMOF—$NH_2$, by a nitrogen atom and bears a function R on one of its constituent carbon atoms. Said reactive group based on said triazole ring thus has the empirical formula —$N_3$—CH—CR. One nitrogen atom of the triazole ring is bound to the organic ligand present in the functionalized solid and derived from an organic ligand present in the solid DMOF—$NH_2$. Said reactive group is represented later in the present description when it is bound to a particular organic ligand, of the terephthalate type. The function R is selected from the following functions: alkane, alkene, alkyne, amine, amide, alcohol, thiol, carboxylic acid, hydroxyl, aldehyde, ketone, phenyl, benzyl, azo (—N=N—R1), diazo (—C=$N^+$=$N^-$), nitrile (—C≡N), imide (—C(=O)—N(—$R_1$)—C(=O)—$R_2$), imine ($R_1$, $R_2$—C=N—$R_3$), ether ($R_1$—O—$R_2$), ester, halogen, isocyanate (—N=C=S), silane, nitro (—$NO_2$), nitroso (—NO), and aromatic heterocycle. Preferably, said function R is selected from the benzyl, phenyl, aromatic heterocycle and amine functions. For example, the function R can be pyridine as aromatic heterocycle.

The functionalized hybrid solid with an organic-inorganic matrix is a solid of three-dimensional structure containing an inorganic network of metallic centres connected by organic ligands, which are identical to those present in the solid MOF—$NH_2$ except for substitution of the —$NH_2$ function with the reactive group based on the triazole ring —$N_3$—CH—CR. Said metallic centres are for example based on aluminium, indium, iron or zinc atoms. Preferably, said organic ligands present in the functionalized solid are ligands derived from the 2-aminoterephthalate ligands —$O_2$C—$C_8H_3$—$NH_2$—$CO_2$ ($NH_2$-bdc ligand) present in the solid MOF—$NH_2$ and consequently have the semi-structural formula —$O_2$C—$C_6H_3$($N_3$—CH—CR)—$CO_2$ (designated $N_3$—CH—CR-bdc) and the structural formula as shown below:

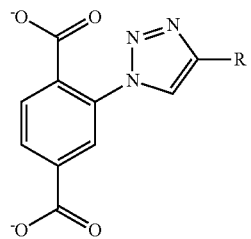

According to the invention, the functionalized solid obtained by the process of the invention has a crystalline structure identical to that of the solid MOF—$NH_2$ from which it is derived.

The crystallized hybrid solid with an organic-inorganic matrix, MOF—$NH_2$, used for implementing said stage i) of the process of preparation according to the invention is a solid of three-dimensional structure containing an inorganic network of metallic sites, for example based on aluminium, indium, iron or zinc atoms, joined together at least by organic ligands comprising at least one aromatic ring, at least two carboxylate functions $CO_2^-$ and at least one amine function —$NH_2$. The metallic sites perform the role of linkers. Preferably, said organic ligands present in said solid MOF—$NH_2$ are formed by the entity 2-aminoterephthalate —$O_2$C—$C_6H_3$—$NH_2$—$CO_2$ ($NH_2$-bdc ligand). Said solid MOF—$NH_2$ can also comprise other types of organic ligands, different from the ligands comprising at least one aromatic ring, at least two carboxylate functions $CO_2^-$ and at least one amine function —$NH_2$. Within the scope of the present invention, the other types of organic ligands are unreactive ligands: they do not compete with the ligands comprising at least one aromatic ring, at least two carboxylate functions $CO_2^-$ and at least one amine function —$NH_2$, in particular they do not compete with the $NH_2$-bdc ligands, so that the functionalization only concerns the function —$NH_2$ present in the ligands comprising at least one aromatic ring, at least two carboxylate functions $CO_2^-$ and at least said amine function —$NH_2$, preferably present in the $NH_2$-bdc ligands, so that the process of the invention permits replacement of the amine function with the reactive group —$N_3$—CH—CR. For example, the solid MOF—$NH_2$ can comprise a first type of organic ligands formed by the entity 2-aminoterephthalate —$O_2$C—$C_6H_3$—$NH_2$—$CO_2$ ($NH_2$-bdc ligand) and a second type of organic ligands formed by the entity 1,4-diazabicyclo[2.2.2]octane (DABCO).

Preferably, said crystallized hybrid solid with an organic-inorganic matrix, MOF—$NH_2$, used for implementing said stage i) of the process of preparation according to the invention, is selected from the solids Fe(OH)($NH_2$-bdc), $Fe_3$O(solv)$_3$Cl($NH_2$-bdc)$_3$, $Zn_3$($NH_2$-bdc)$_3$($H_2$O)$_2$, $Zn_2$($NH_2$-bdc)$_2$(dabco), Al(OH)($NH_2$-bdc), $Al_4$(OH)$_2$(OCH$_3$)$_4$($NH_2$-bdc)$_3$ $Zn_4$O($NH_2$-bdc)$_3$ and In(OH)($NH_2$-bdc). The solids Fe(OH)($NH_2$-bdc) and $Fe_3$O(solv)$_3$Cl($NH_2$-bdc)$_3$, where solv=$H_2$O, DMF, are known in the literature respectively by the names Fe-MIL-53-$NH_2$ and Fe-MIL-101-$NH_2$ (S. Bauer; C. Serre; T. Devic; P, Horcajada; J. Marrot; G. Ferey, N. Stock, *Inorganic Chemistry*, 2008, 47, 7568-7576). Their process of preparation is also described there. The solid $Zn_3$($NH_2$-bdc)$_3$($H_2$O)$_2$ is known in the literature (X.-F. Wang; Y.-B. Zhang; X.-N. Cheng, X.-M. Chen, *CrystEngComm*, 2008, 10, 753-758). Its process of preparation is also described there. The solid $Zn_2$($NH_2$-bdc)$_2$(dabco) is known in the literature by the name DMOF-1-$NH_2$ (Z. Q. Wang; K. K. Tanabe, S. M. Cohen, *Inorganic Chemistry*, 2009, 48, 296-306). Its process of preparation is also described there. The solid Al(OH)($NH_2$-bdc) is known in the literature by the name Al-MIL-53-$NH_2$ (T. Ahnfeldt; D. Gunzelmann; T. Loiseau; D. Hirsemann; J. R. Senker; G. Ferey, N. Stock, 2009, *Inorganic Chemistry*, 48, 7, 3057-3064). Its process of preparation is also described there. The solid $Al_4$(OH)$_2$(OCH$_3$)$_4$($NH_2$-bdc)$_3$ is known in the literature by the name CAU-1 (T. Ahnfeldt, N. Guillou, D. Gunzelmann, I. Margiolaki, T. Loiseau, G. Ferey, J. Senker, N. Stock, *Angew. Chem. Int. Ed*, 2009, Vol. 48, No. 28, 5163-5166). Its process of preparation is also described there. The solid $Zn_4$O($NH_2$-bdc)$_3$ is known in the literature by the name IRMOF-3-$NH_2$ (M. Eddaoudi; J. Kim; N. Rosi; D. Vodak; J. Wachter; M. O'Keefe, O. M. Yaghi, *Science*, 2002, 295, 469-472). Its process of preparation is also described there. The solid In(OH)($NH_2$-bdc), called IHM-2, has a crystalline structure isostructural with that of the materials MIL-68 known and described in the literature (T. Loiseau et al., *Inorganic Chemistry*, 2008, 47, 11892-11901). The X-ray diffraction pattern of the solid IHM-2 is shown in FIG. 1. A process for preparing said solid In(OH)(NH$_2$-bdc) is given as an example in the "Examples" section of the present patent application.

According to said stage i) of said process for the preparation of the functionalized solid according to the invention, said crystallized hybrid solid MOF—NH$_2$ is previously dried before being introduced into said polar solvent S1. The drying of said crystallized hybrid solid MOF—NH$_2$ is advantageously carried out at a temperature between 20 and 100° C. for a time between 1 and 24 hours, very advantageously for a time of about 12 hours. Drying is carried out in air or under vacuum, preferably under vacuum.

According to said stage i) of the process of preparation according to the invention, said organic compound Q containing a nitride function N$_3$ is advantageously selected from trimethylsilyl nitride (TMS-N$_3$, (CH$_3$)$_3$SiN$_3$), triflyl nitride (TfN$_3$, where Tf=CF$_3$SO$_2$), p-tosyl nitride (TsN$_3$, or 4-methylbenzenesulphonylazide of formula C$_6$H$_4$(CH$_3$)SO$_2$N$_3$) and sodium nitride (NaN$_3$). Preferably, said organic compound containing a function N$_3$ is trimethylsilyl nitride (TMS-N$_3$).

According to said stage i) of the process of preparation according to the invention, said intermediate reagent R containing a nitrite function NO$_2$ is advantageously selected from alkaline reagents such as sodium nitrite (NaNO$_2$) and calcium nitrite (Ca(NO$_2$)$_2$), metallic reagents and reagents of the alkyl type such as tert-butyl-nitrite (tBuONO, (CH$_3$)$_3$CONO). Very preferably, said intermediate reagent R containing a nitrite function NO$_2$ is tert-butyl-nitrite (tBuONO). Said intermediate reagent R containing a nitrite function NO$_2$ ensures the formation of a diazonium salt, which then reacts with the organic compound Q.

The polar solvent S1 used for implementing said stage i) of the process of preparation according to the invention is preferably volatile. It is very advantageously selected from tetrahydrofuran (THF), ethanol and acetonitrile.

According to said stage i) of the process of preparation according to the invention, the reaction mixture preferably has the following molar composition, based on one molar equivalent of the —NH$_2$ function present in the solid MOF—NH$_2$:

1MOF—NH$_2$:4-100R:1-90Q:100-400S1

According to said stage ii) of the process of preparation according to the invention, said reaction stage is preferably carried out at a temperature between 0 and 60° C., and even more preferably at ambient temperature. The reaction mixture is stirred with a magnetic stirrer. The reaction time is between 1 and 24 hours, preferably between 5 and 15 hours, most often about 12 hours.

According to said stage iii) of the process of preparation according to the invention, reagent A, also called graft as it permits the grafting of the reactive group on the solid MOF—NH$_2$ by a method of "one pot" post-modification functionalization, comprises simultaneously at least one alkyne or activated cyanide COCN terminal function and a function R, where R is defined as described previously, namely R is selected from the following functions: alkane, alkene, alkyne, amine, amide, alcohol, thiol, carboxylic acid, hydroxyl, aldehyde, ketone, phenyl, benzyl, azo, diazo, nitrile, imide, imine, ether, ester, halogen, isocyanate, silane, nitro, nitroso, aromatic heterocycle. Preferably, said function R is selected from the benzyl, phenyl, aromatic heterocycle and amine functions. For the implementation of said stage iii), it is possible for example to use, as the grafting reagent A, a compound selected from 1-butyne (CH$_3$—CH$_2$—CCH), propargyl amine (NH$_2$—CH$_2$—CCH), 2-propyn-1-ol ((OH)—CH$_2$—CCH), 3-butyn-2-one (CH$_3$—CO—CCH), N-methylpropargyl amine (CH$_3$—NH—CH$_2$—CCH), propiolic acid (COOH—CCH), methylpropargyl ether (CH$_3$—CH$_2$—O—CCH), propargyl chloride (Cl—CH$_2$—CCH), 2-methyl-3-butyn-2-amine ((NH$_2$)(CH$_3$)$_2$—C—CCH), 3-dimethylamino-1-propyne (N(CH$_3$)$_2$(CH$_2$CCH), methyl propiolate (CH$_3$O(O)—CCH), phenylacetylene, 2-ethynylpyridine (C$_6$H$_5$CCH), diethylpropargyl amine ((CH$_3$CH$_2$)$_2$N(CH$_2$CCH), benzoyl cyanide (C$_6$H$_5$COCN) and pyruvonitrile (CH$_3$—COCN). Preferably, said reagent A is selected from phenylacetylene, 2-ethynylpyridine (C$_6$H$_5$CCH), diethylpropargyl amine ((CH$_3$CH$_2$)$_2$N—CH$_2$CCH) and benzoyl cyanide (C$_6$H$_5$COCN).

Very advantageously, the terminal function present in said reagent A is an alkyne function.

According to a particular embodiment of the process of the invention, said stage iii) is carried out in the presence of several grafting reagents A each having a function R different from one another. For example, a compound comprising a phenyl function and a terminal alkyne function and a compound comprising an amine function and a terminal alkyne function can be introduced into the reaction mixture obtained from said stage ii). Thus, the process of preparation according to the invention makes it possible to obtain a functionalized solid having several different functions R borne by different reactive groups, each based on a triazole ring.

According to said stage iii), the copper-based catalyst C is selected from the copper compounds having an oxidation number of the copper equal to 1 (Cu(I)) or having an oxidation number of the copper equal to 2 (Cu(II)) in the presence of a reducing agent. Preferably, said catalyst C is selected from the copper compounds having an oxidation number of the copper equal to 1 and more particularly said catalyst C based on Cu(I) is selected from copper acetate (Cu(O)OCH$_3$), copper bromide (CuBr), copper chloride (CuCl), copper cyanide (CuCN), copper iodide (CuI), copper oxide (Cu$_2$O), copper sulphide (Cu$_2$S) and copper tetrakis(acetonitrile) hexafluorophosphate. Preferably, said catalyst C is copper tetrakis(acetonitrile)hexafluorophosphate (Cu$^I$(CH$_3$CN)$_4$PF$_6$).

When said stage iii) is carried out in the presence of a catalyst C based on Cu(II), a catalyst is advantageously selected from copper acetate (Cu((O)OCH$_3$)$_2$), copper acetinolate (Cu(CH$_3$OCHOCH$_3$)$_2$), copper bromide (CuBr$_2$), copper chloride (CuCl$_2$), copper fluoride (CuF$_2$) and copper sulphate (CuSO$_4$). Preferably, said catalyst C based on Cu(II) is copper sulphate (CuSO$_4$). When carried out in the presence of a catalyst C based on Cu(II), said stage iii) is carried out in the presence of a reducing agent. The reducing agent used is preferably sodium ascorbate.

The polar solvent S2 used for implementing said stage iii) of the process of preparation according to the invention is preferably volatile. It is selected very advantageously from tetrahydrofuran (THF) and acetonitrile. The polar solvents S1 and S2 are selected with the same chemical composition or with a different chemical composition. Advantageously, S1 and S2 have the same chemical composition. However, another advantageous case comprises carrying out said stage i) in the presence of ethanol (S1) and said stage iii) in the presence of THF (S2).

According to said stage iii) of the process of preparation according to the invention, the reaction mixture preferably has the following molar composition, based on one molar equivalent of the —NH$_2$ function present in the starting solid MOF—NH$_2$:

1MOF—NH$_2$:0.1-4C:4-100R:1-90Q:1-100A:100-600
(S1+S2)

According to the process of preparation according to the invention, said stage ii) leads to the formation in-situ of a solid in the form of nitride in which the —NH$_2$ function borne by each of said organic ligands present in the solid MOF—NH$_2$ is substituted with the nitride function N$_3$. Said solid in the form of nitride is a synthesis intermediate, which is not isolated. The reagents A, said copper-based catalyst C and said solvent S2 are introduced directly in the reaction mixture comprising said solid intermediate as well as an excess of compound Q and of reagent R. The process of preparation according to the invention is based on a "one pot" method of post-modification functionalization.

According to said stage iv) of the process of preparation according to the invention, said reaction stage is preferably carried out at a temperature between 0 and 60° C., and even more preferably at ambient temperature. The reaction mixture is stirred with a magnetic stirrer. The reaction time is between 1 and 48 hours, preferably between 1 and 24 hours, most often about 12 hours.

According to said stage v) of the process of preparation according to the invention, said crystallized functionalized hybrid solid obtained at the end of said stage iv) is filtered and then washed with suitable solvents. Washing of said crystallized functionalized hybrid solid is preferably carried out by a first sequence of washings using polar solvents, for example THF, followed by a second sequence of washings using volatile solvents, for example dichloromethane. For example, the stage of washing of said crystallized functionalized hybrid solid can comprise 3 sequences of washing with THF followed by 3 sequences of washing with dichloromethane CH$_2$Cl$_2$.

According to said stage vi) of the process of preparation according to the invention, said crystallized functionalized hybrid solid is dried. Drying is carried out in air or under vacuum between 20° C. and 100° C. Preferably, drying is carried out at ambient temperature under vacuum for a time in the range from 1 to 24 hours, most often about 12 hours.

The functionalized solid obtained at the end of said stage vi) is analysed by X-ray diffraction, by Fourier transform infrared spectroscopy (FTIR) and by proton nuclear magnetic resonance ($^1$H NMR). These analyses demonstrate the effectiveness of the post-modification functionalization treatment according to the invention. In particular, analysis of the crystallized functionalized hybrid solid by XRD demonstrates that the post-modification functionalization treatment for replacing the amino function —NH$_2$ with the reactive group —N$_3$—CH—CR does not affect the structure and the crystallinity of the solid. Analysis by FTIR reveals the absence of the amino function —NH$_2$ on the organic ligands, which are reactive with respect to the reactions applied in stages ii) and iv) of the process of the invention and are present in the functionalized solid. Depending on circumstances, when the reaction applied in said stage iv) does not go to completion, FTIR analysis of the functionalized solid resulting from said stage yl) may reveal the presence of the nitride function formed during application of said stage ii) of the process of the invention, and said nitride function may thus be present in a proportion of the organic ligands present in the functionalized solid, which also has ligands with the reactive group —N$_3$—CH—CR. When combined with FTIR analysis, analysis by $^1$H NMR confirms the absence of the amino function —NH$_2$ on each of the organic ligands, which are reactive with respect to the reactions employed in stages ii) and iv) of the process of the invention and are present in the functionalized solid, and makes it possible to estimate the degree of modification of the amino functions —NH$_2$ to the reactive group —N$_3$—CH—CR. According to the process of preparation according to the invention, this degree of modification of the —NH$_2$ functions to reactive group —N$_3$—CH—CR is very high, i.e. equal to at least 95%, preferably equal to at least 98% or even very often equal to 100%. In the case when the reaction applied in said stage iv) does not go to completion, the functionalized solid has both unreacted nitride functions N$_3$ and reactive groups —N$_3$—CH—CR. The degree of modification of the nitride functions N$_3$ to reactive groups —N$_3$—CH—CR is calculated by quantifying the decrease in relative area of the signals of the aromatic protons of the intermediate solid relative to those of the functionalized solid. The $^1$H NMR spectrum of the functionalized solid has new signals, connected in particular with the appearance of a singlet integrating for one proton, which corresponds to the proton borne by the triazole ring (N$_3$—CH—CR).

According to the process of the invention, the degree of modification of the nitride functions N$_3$ to reactive groups —N$_3$—CH—CH depends on the application (operating conditions and molar composition) of stages iii) and iv): in particular, for a given grafting reagent A, the degree of modification of the nitride functions N$_3$ to reactive groups —N$_3$—CH—CR will increase as the number of molar equivalents of reagent A and of the catalyst C introduced in stage iii) increases and/or as the reaction time of said stage iv) increases. When the reaction applied in said stage iv) goes to completion (degree of modification of N$_3$ to N$_3$—CH—CR=100%), each of the organic ligands present in the solid MOF—NH$_2$ and comprising at least one aromatic ring, at least two carboxylate functions and at least one amine function is substituted with as many organic ligands comprising at least one aromatic ring, at least two carboxylate functions and at least one reactive group N$_3$—CH—CR in the functionalized solid obtained by the process of the invention. When the reaction applied in said stage iv) does not go to completion (degree of modification of N$_3$ to N$_3$—CH—CR<100%), the organic ligands present in the solid MOF—NH$_2$ and comprising at least one aromatic ring, at least two carboxylate functions and at least one amine function are replaced with 2 types of ligands with different reactive functions: organic ligands comprising at least one aromatic ring, at least two carboxylate functions and at least one reactive group N$_3$—CH—CR and organic ligands comprising at least one aromatic ring, at least two carboxylate functions and at least one —N$_3$ function. Thus, one of the advantages of the process of the present invention is that it is possible to control the degree of modification of the nitride functions N$_3$ to reactive groups —N$_3$—CH—CR, which may be beneficial depending on the applications envisaged for the functionalized solid. In fact, depending on the application envisaged for the functionalized solid, a person skilled in the art will seek to obtain either a functionalized solid in which each of the ligands bears the reactive group —N$_3$—CH—CR (degree of modification of N$_3$ to N$_3$—CH—CR=100%) or a functionalized solid in which some of the organic ligands bear an —N$_3$ function and others bear said reactive group —N$_3$—CH—CR (degree of modification of N$_3$ to N$_3$—CH—CR<100%).

EXAMPLES

The crystallized hybrid solids MOF—NH$_2$ and the functionalized solids, obtained by application of the syntheses illustrated in the following examples, were analysed by X-ray diffraction, by Fourier transform infrared spectroscopy (FTIR) and by proton nuclear magnetic resonance ($^1$H NMR). The intermediate solids bearing the nitride function $N_3$, present in the reaction mixture at the end of application of said stage ii) of the process of preparation according to the invention, are also analysed by X-ray diffraction, by Fourier transform infrared spectroscopy (FTIR) and by proton nuclear magnetic resonance ($^1$H NMR).

The X-ray diffraction patterns are obtained by radiocrystallographic analysis using the classical powder technique with a Bruker D5005 diffractometer (CuK$\alpha_{1+2}$=0.15418 nm) equipped with a graphite-curved rear monochromator and a scintillation detector. The analyses of the solids were recorded in Debye-Scherrer mode from 3 to 80° (2θ) in steps of 0.02° for 8 seconds.

The infrared analyses are carried out using KBr tablets on a Vector 22 Bruker FTIR instrument with a useful operating range of: 4000-400 cm$^{-1}$.

The spectra from nuclear magnetic resonance in solution are obtained using a Bruker Avance 250 NMR Spectrometer (5.87 T, 250 MHz for 1H).

Example 1

Preparation of Functionalized Solids from the Crystallized Hybrid Solid DMOF-1-NH$_2$ Example 1.1

Preparation of the Crystallized Hybrid Solid DMOF-1-NH$_2$ 0.781 g of zinc nitrate Zn(NO$_3$)$_2$.4H$_2$O (3.00 mmol, Merck, 98.5%) and 0.554 g of 2-amino-1,4-benzene dicarboxylic acid NH$_2$—BDC (3.03 mmol, Alfa Aesar, 99%) are dissolved in 75 mL of dimethylformamide (DMF, Aldrich, 99.8%). 0.542 g of 1,4-diazabicyclo[2.2.2]octane DABCO (4.815 mmol, Aldrich, 98%) is then added to the solution. This addition results in the immediate appearance of a white precipitate. The precipitate obtained is filtered on a frit of low porosity and the filtrate is recovered and diluted with 75 mL of DMF. The solution constituted by the filtrate is then divided into 5 aliquots of 30 mL which are distributed in 5 stainless steel autoclaves (capacity 43 mL) and heated from 35 to 120° C. with a ramp of 2.5° C./min. The temperature is maintained at 120° C. for 12 hours. This procedure gives yellowish crystals in the form of small rods of DMOF-1-NH$_2$. The mother liquor is left to settle and the crystals are washed three times with 6 mL of DMF and then three times with 6 mL of CH$_2$Cl$_2$ (Acros Organics, 99.99%). The crystals are then left in suspension in 10 mL of CH$_2$Cl$_2$ for 3 days, renewing the solvent every 24 hours. Finally, the crystals are dried under vacuum at ambient temperature overnight. 300 mg of DMOF-1-NH$_2$ is thus obtained, representing a yield of 35% based on the starting Zn(NO$_3$)$_2$.4H$_2$O.

Said crystallized hybrid solid DMOF-1-NH$_2$ is analysed by X-ray diffraction, by Fourier transform infrared spectroscopy and by proton nuclear magnetic resonance ($^1$H NMR).

Analysis by X-ray diffraction reveals that said solid thus obtained is identified as being constituted by solid DMOF-1-NH$_2$: the diffraction pattern obtained from said solid is identical to that presented in *Inorganic Chemistry*, 2009, 48, 300.

Analysis by FTIR reveals the presence of the amino function —NH$_2$ in the solid DMOF-1-NH$_2$. IR (KBr tablet), ν (cm$^{-1}$): 3454, 3344, 2958, 1632, 1666, 1577, 1435, 1376, 1256, 1056, 833, 810, 772, 704, 661, 593. The bands at 3454 and 3344 cm$^{-1}$ are attributed to the amine function.

$^1$H NMR analysis is carried out on a sample of the solid DMOF-1-NH$_2$, after digestion and complete dissolution of the sample in a deuterated mixture DCl/D$_2$O/DMSO-d$_6$ according to the procedure described in the literature (Z. Q. Wang, S. M. Cohen, *Journal of the American Society*, 2007, 129, 12368-12369): 10 mg of hybrid solid DMOF-1-NH$_2$ is digested and dissolved in 1.5 mL of deuterated DMSO and 0.2 mL of a dilute solution of DCl (prepared from a solution containing 0.23 mL of DCl/D$_2$O at 35% and 1 mL of deuterated DMSO).

$^1$H NMR analysis also reveals the presence of the amino group —NH$_2$ in the solid DMOF-1-NH$_2$. $^1$H NMR, 250 Hz, rt, δ (ppm/(DCl/D$_2$O/DMSO-d$_6$)): 7.02 (d, 1H, J=8.3 Hz); 7.38 (s, 1H); 7.74 (d, 1H, J=8.3 Hz), 3.52 (s, 6H, DABCO).

$^1$H NMR analysis also confirms the presence of the ligands NH$_2$-bdc and DABCO in proportions such that the molar ratio NH$_2$-bdc/DABCO=2.

Example 1.2

Preparation of a Functionalized Solid Bearing a Phenyl Function on the Triazole Ring, Using Phenylacetylene as Reagent with Alkyne Terminal Function 80 mg (0.27 mmol equivalent —NH$_2$) of solid DMOF-1-NH$_2$ obtained at the end of the procedure presented in Example 1.1 is dried for 12 hours at 85° C. under vacuum and is then placed in a pill machine (capacity 8 mL) with 3 mL (37 mmol, 137 eq) of THF, 0.217 mL (1.84 mmol, 7 eq) of tBuONO (Aldrich) and 0.199 mL (1.508 mmol, 6 eq) of TMS-N$_3$ (Aldrich). After reaction overnight at ambient temperature and with stirring, 0.96 mL of phenylacetylene (8.8 mmol, 32 eq, Aldrich, 98%) and 48 mg of Cu$^I$(CH$_3$CN)$_4$PF$_6$ (0.26 mmol, 1 eq, Aldrich) in solution in 1 mL of THF (12.3 mmol, 46 eq) are added and the mixture is stirred for a further 12 h at ambient temperature. After filtration, the solid is washed 3 times with THF (×8 ml) and then 3 times with CH$_2$Cl$_2$ (×8 ml). The solid is finally dried under vacuum at ambient temperature overnight.

The solid obtained was analysed by X-ray diffraction. The diffraction pattern obtained on the DMOF-1-functionalized solid shows that said solid has a crystalline structure identical to that of the solid DMOF-1-NH$_2$. XRD analysis carried out on the crystallized hybrid DMOF-1-functionalized solid demonstrates that the post-modification treatment for replacing the amino function —NH$_2$ with the reactive group —N$_3$CHCC$_6$H$_5$ does not affect the structure and the crystallinity of the solid.

In order to quantify the degree of modification of DMOF-1-NH$_2$ to DMOF-1-functionalized and of DMOF-1-N$_3$ (intermediate solid that is not isolated) to DMOF-1-functionalized, these solids are analysed by $^1$H-NMR. $^1$H NMR analysis is carried out on a sample of the hybrid DMOF-1-functionalized solid, after digestion and complete dissolution of the sample in a deuterated mixture DCl/D$_2$O/DMSO-d$_6$ according to a procedure described in the literature (Z. Q. Wang, S. M. Cohen, *Journal of the American Chemical Society*, 2007, 129, 12368-12369): 10 mg of hybrid DMOF-1-functionalized solid is digested and dissolved in 1.5 mL of deuterated DMSO and 0.2 mL of a dilute solution of DCl (prepared from a solution containing 0.23 mL of DCl/D$_2$O at 35% and 1 mL of deuterated DMSO).

$^1$H NMR analysis confirms the presence of the reactive group —N$_3$CHCC$_6$H$_5$ on the aromatic ring of the terephthalate ligand. $^1$H NMR 250 MHz, rt, δ (ppm/(DCl/D$_2$O/DMSO-d$_6$)): δ=9.14 (s, 1H), 8.19 (m, 2H), 8.05 (d, 1H, J=8 Hz.), 7.93 (d, 2H, J=7 Hz), 7.45 (m, 3H), 3.52 (s, 6H, DABCO). Detection of a singlet at 9.14 ppm corresponds to the proton borne by the triazole ring —N$_3$CHCC$_6$H$_5$—.

$^1$H NMR analysis also confirms the presence of the ligands N$_3$CHCR-bdc and DABCO in the same proportions such that the molar ratio N$_3$CHCR-bdc/DABCO=2.

Analysis by FTIR reveals that the bands at 3454 and 3344 cm$^{-1}$ corresponding to the —NH$_2$ function have completely disappeared.

Comparison of the IR and $^1$H NMR spectra obtained for the solids DMOF-1-NH$_2$, DMOF-1-N$_3$ and DMOF-1-functionalized (DMOF-1-N$_3$—CH—CC$_6$H$_5$) demonstrates the efficacy of said post-modification functionalization treatment, and comparison of the $^1$H NMR spectra obtained for the solid DMOF-1-NH$_2$ and for the DMOF-1-functionalized solid makes it possible to determine a 100% degree of modification of the amino functions —NH$_2$ to reactive groups —N$_3$CHCC$_6$H$_5$ by quantifying the decrease in relative area of the signals from the solid DMOF-1-NH$_2$ relative to those from the solid DMOF-1-N$_3$—CH—CC$_6$H$_5$. Comparison of the $^1$H NMR spectra obtained for the solid DMOF-1-N$_3$ and for the DMOF-1-functionalized solid (DMOF-1-N$_3$—CH—CC$_6$H$_5$) also finds 100% degree of modification of the nitride functions N$_3$ to reactive groups —N$_3$CHCC$_6$H$_5$ by quantifying the decrease in relative area of the signals of the solid DMOF-1-N$_3$ relative to those of the functionalized solid DMOF-1-N$_3$—CH—CC$_6$H$_5$.

Moreover, positive-mode mass spectrometry carried out on the functionalized solid DMOF-1-N$_3$—CH—CC$_6$H$_5$ shows a peak at m/z 310, which corresponds to the functionalized ligand (2-(-4-phenyl-1,2,3-triazol-1-yl) terephthalic acid.

Example 1.3

Preparation of a Functionalized Solid Bearing a Tertiary Amine Function on the Triazole Ring, Using Diethylpropargyl Amine as Reagent with Alkene Terminal Function This example is carried out in the same operating conditions as Example 1.2. Diethylpropargyl amine (CH$_3$CH$_2$)$_2$—N—CH$_2$—CCH is used instead of phenylacetylene. The quantities of each of the reagents introduced are as follows:
Stage i):
DMOF-1-NH$_2$: 80 mg (0.27 mmol equivalent —NH$_2$); THF: 3 mL (37 mmol, 137 eq); tBuONO: 0.217 mL (1.84 mmol, 7 eq); TMS-N$_3$: 0.199 mL (1.508 mmol, 6 eq).
Stage iii):
diethylpropargyl amine: 0.33 mL (2.3 mmol, 8.5 eq); Cu$^I$(CH$_3$CN)$_4$PF$_6$: 21 mg (0.11 mmol, 0.4 eq); THF: 1 ml (12.3 mmol, 46 eq)

The DMOF-1-functionalized solid obtained was analysed by X-ray diffraction. The diffraction pattern obtained on the DMOF-1-functionalized solid shows that said solid has a crystalline structure identical to that of the solid DMOF-1-NH$_2$. XRD analysis carried out on the crystallized hybrid DMOF-1-functionalized solid shows that the post-modification functionalization treatment for replacing the amino function —NH$_2$ with the reactive group —N$_3$CH—C—CH$_2$—N—(CH$_2$—CH$_3$)$_2$ does not affect the structure and the crystallinity of the solid.

The functionalized solid DMOF-1-N$_3$CH—C—CH$_2$—N—(CH$_2$—CH$_3$)$_2$ is also analysed by FTIR and $^1$H NMR in the same way as described in Example 1.2. Comparison of the FTIR and $^1$H NMR spectra obtained for the solids DMOF-1-NH$_2$ and DMOF-1-N$_3$CH—C—CH$_2$—N—(CH$_2$—CH$_3$)$_2$ finds 100% degree of modification of the amino functions —NH$_2$ to reactive groups —N$_3$CH—C—CH$_2$—N—(CH$_2$—CH$_3$)$_2$. The degree of modification of the nitride functions N$_3$ to reactive groups is shown in Table 1.

Example 1.4

Preparation of a Functionalized Solid Bearing a Function Constituted by a Heterocycle C$_5$H$_4$N on the Triazole Ring Using the Reagent 2-Ethynylpyridine as Reagent with Alkene Terminal Function This example is carried out following the same procedure as in Example 1.2. 2-Ethynylpyridine (C$_5$H$_4$N)CCH is used instead of phenylacetylene.
The quantities of each of the reagents introduced are as follows:
Stage i):
DMOF-1-NH$_2$: 80 mg (0.27 mmol equivalent —NH$_2$); THF: 3 mL (37 mmol, 137 eq); tBuONO: 0.217 mL (1.84 mmol, 7 eq); TMS-N$_3$: 0.199 mL (1.508 mmol, 6 eq).
Stage iii):
2-ethynylpyridine: 2 ml (19.8 mmol, 73 eq); Cu$^I$(CH$_3$CN)$_4$PF$_6$: 109 mg (0.59 mmol, 2.2 eq); THF: 1 ml (12.3 mmol, 46 eq).

The DMOF-1-functionalized solid obtained was analysed by X-ray diffraction. The diffraction pattern obtained on the DMOF-1-functionalized solid shows that said solid has a crystalline structure identical to that of the solid DMOF-1-NH$_2$. XRD analysis carried out on the crystallized hybrid DMOF-1-functionalized solid demonstrates that the post-modification functionalization treatment for replacing the amino function —NH$_2$ with the reactive group —N$_3$CH—C—C$_5$H$_4$N does not affect the structure and the crystallinity of the solid.

The functionalized solid DMOF-1-N$_3$CH—C—C$_5$H$_4$N is also analysed by FTIR and $^1$H NMR in the same way as described in Example 1.2. Comparison of the FTIR and $^1$H NMR spectra obtained for the solid DMOF-1-NH$_2$ and DMOF-1-N$_3$CH—C—C$_5$H$_4$N provides an estimate of 100% degree of modification of the amino functions —NH$_2$ to reactive groups —N$_3$CH—C—C$_5$H$_4$N. The degree of modification of the nitride functions N$_3$ to reactive groups —N$_3$CH—C—C$_5$H$_4$N is shown in Table 1.

Example 2

Preparation of Functionalized Solids from the Crystallized Hybrid Solid MIL-53-Al—NH$_2$

Example 2.1

Preparation of the Crystallized Hybrid Solid MIL-53-Al—NH$_2$ 120 mg (0.66 mmol) of 2-amino-1,4-benzene dicarboxylic acid (Alfa Aesar, 99%) in suspension in 28 mL (1.55 mmol) of distilled water is placed in a PTFE vessel of 40 mL capacity, 1.10 mL (0.44 mmol) of a solution of hydrated aluminium chloride (AlCl$_3$.6H$_2$O, Aldrich, 98%) at a concentration of 0.4 mol/L and 0.56 mL (0.22 mmol) of a solution of NaOH at a concentration of 0.4 mol/L are added. The mixture is stirred for 5 minutes with a magnetic stirrer. The PTFE vessel is then transferred to an autoclave and then heated without stirring at 110° C. for 24 h. After cooling, the crystalline solid obtained is washed with water, then with hot DMF solution (Aldrich, 99.8%) and with dichloromethane (ACROS ORGANIGS, 99.99%). After stove drying (air) at 80° C. overnight, a powder constituted by crystals of MIL-53-Al—NH$_2$ is obtained.

Said crystallized hybrid solid MIL-53-Al—NH$_2$ is analysed by X-ray diffraction, by Fourier transform infrared spectroscopy and by proton nuclear magnetic resonance ($^1$H NMR).

X-ray diffraction analysis reveals that said solid thus obtained is identified as being constituted by solid MIL-53-Al—NH$_2$: the diffraction pattern obtained on said solid is identical to that corresponding to the solid MIL-53-Al—NH$_2$ (It) described in *Inorganic Chemistry*, 2009, 48, 7, 3057-3064.

Analysis by FTIR reveals the presence of the amino function —NH$_2$ in the solid MIL-53-Al—NH$_2$.

IR (KBr tablet), ν (cm$^{-1}$): 3498, 3386, 2951, 1685, 1581, 1487, 1436, 1402, 1333, 1256, 1000, 777, 640, 597, 546, 452. The bands at 3498 and 3386 cm$^{-1}$ are attributed to the amine function.

$^1$H NMR analysis is carried out on a sample of the solid MIL-53-Al—NH$_2$, after digestion and complete dissolution of the sample in a deuterated mixture DCl/D$_2$O/DMSO-d$_6$ according to the procedure described in the literature (Z. Q. Wang, S. M. Cohen, *Journal of the American Society*, 2007, 129, 12368-12369): 10 mg of hybrid solid MIL-53-Al—NH$_2$ is digested and dissolved in 1.5 ml of deuterated DMSO and 0.2 mL of a dilute solution of DCl (prepared from a solution containing 0.23 mL of DCl/D$_2$O at 35% and 1 mL of deuterated DMSO).

Combined with analysis by FTIR, $^1$H NMR analysis also reveals the presence of the amino group —NH$_2$ in the solid MIL-53-Al—NH$_2$. $^1$H NMR, 250 MHZ, rt, δ (ppm/(DCl/D$_2$O/DMSO-d$_6$)): 6.90 (d, 1H, J=8 Hz); 7.03 (s, 1H); 7.56 (d, 1H, J=8 Hz).

Example 2.2

Preparation of a Functionalized Solid Bearing a Phenyl Function on the Triazole Ring, Using Phenylacetylene as Reagent with Alkene Terminal Function 80 mg (0.36 mmol equivalent —NH$_2$) of solid MIL-53-Al-1-NH$_2$ obtained at the end of the procedure described in Example 2.1 is dried for 12 hours at 85° C. under vacuum and is then placed in a pill machine (capacity 8 mL) with 3 mL (51.3 mmol, 142.5 eq) of ethanol, 3.8 ml (32 mmol, 89 eq) of tBuONO (Aldrich) and 3.6 mL (28 mmol, 78 eq) of TMS-N$_3$ (Aldrich).

After reaction overnight at ambient temperature and with stirring, 0.78 mL of phenylacetylene (7.2 mmol, 20 eq, Aldrich, 98%) and 51 mg of Cu$^I$(CH$_3$CN)$_4$PF$_6$ (0.28 mmol, 0.8 eq, Aldrich) in solution in 1 mL of THF (17.1 mmol, 47.5 eq) are added and the mixture is stirred for a further 12 h at ambient temperature. After filtration, the solid is washed 3 times with THF (×8 ml) and then 3 times with CH$_2$Cl$_2$ (×8 ml). The solid is finally dried under vacuum at ambient temperature overnight.

The MIL-53-Al-functionalized solid obtained was analysed by X-ray diffraction. The diffraction pattern obtained on the MIL-53-Al-functionalized solid shows that said solid has a crystalline structure identical to that of the solid MIL-53-Al—NH$_2$. XRD analysis carried out on the crystallized hybrid MIL-53-Al-functionalized solid demonstrates that the post-modification functionalization treatment for replacing the amino function —NH$_2$ with the reactive group —N$_3$CH—OC$_6$H$_5$ does not affect the structure and the crystallinity of the solid.

The functionalized solid MIL-53-Al—N$_3$—CH—C—C$_6$H$_5$ is also analysed by FTIR and $^1$H NMR in the same way as described in Example 1.2. Comparison of the FTIR and $^1$H NMR spectra obtained for the solids MIL-53-Al—NH$_2$ and MIL-53-Al—N$_3$—CH—C—C$_6$H$_5$ provides an estimate of 100% as the degree of modification of the amino functions —NH$_2$ to reactive groups —N$_3$CH—C—C$_6$H$_5$. The degree of modification of the nitride functions N$_3$ to reactive groups is shown in Table 1.

Example 2.3

Preparation of a Functionalized Solid Bearing a Function Constituted by a Heterocycle C$_5$H$_4$N on the Triazole Ring Using the Reagent 2-Ethynylpyridine as Reagent with Alkyne Terminal Function This example is carried out following the same procedure as in Example 2.2. 2-Ethynylpyridine (C$_5$H$_4$N)CCH is used instead of phenylacetylene.

The quantities of each of the reagents introduced are as follows:
Stage i):
MIL-53-Al—NH$_2$: 80 mg (0.36 mmol equivalent —NH$_2$); ethanol: 3 mL (51.3 mmol, 142.5 eq); tBuONO; 3.8 mL (32 mmol, 89 eq); TMS-N$_3$: 3.6 mL (28 mmol, 78 eq)
Stage iii):
2-ethynylpyridine: 1.28 ml (12.6 mmol, 35 eq); Cu$^I$(CH$_3$CN)$_4$PF$_6$: 48 mg (0.26 mmol, 0.7 eq); THF: 1 ml (17.1 mmol, 47.5 eq).

The MIL-53-Al-functionalized solid obtained was analysed by X-ray diffraction. The diffraction pattern obtained on the MIL-53-Al-functionalized solid shows that said solid has a crystalline structure identical to that of the solid MIL-53-Al—NH$_2$. XRD analysis carried out on the crystallized hybrid MIL-53-Al-functionalized solid demonstrates that the post-modification functionalization treatment for replacing the amino function —NH$_2$ with the reactive group —N$_3$CH—C—C$_6$H$_4$N does not affect the structure and the crystallinity of the solid.

The functionalized solid MIL-53-Al—N$_3$CH—C—C$_5$H$_4$N is also analysed by FTIR and $^1$H NMR in the same way as described in Example 1.2. Comparison of the FTIR and $^1$H NMR spectra obtained for the solids MIL-53-Al—NH$_2$ and MIL-53-Al—N$_3$CH—C—C$_5$H$_4$N provides an estimate of 100% as the degree of modification of the amino functions —NH$_2$ to reactive groups —N$_3$CH—C—C$_5$H$_4$N. The degree of modification of the nitride functions N$_3$ to reactive groups —N$_3$CH—C—C$_5$H$_4$N is shown in Table 1.

Example 3

Preparation of Functionalized Solids from the Crystallized Hybrid Solid CAU-1

Example 3.1

Preparation of the Crystallized Hybrid Solid CAU-1

365.3 mg of hydrated aluminium chloride (AlCl$_3$.6H$_2$O, 1.5 mmol, Aldrich, 98%) is put in a PTFE vessel of 40 mL capacity, and 94 mg of 2-aminoterephthalic acid (NH$_2$—H$_2$-bdc, 0.5 mmol, Alfa Aesar, 99%) and 10 mL of methanol (ACROS ORGANICS, 99.99%) are added. The mixture is stirred for 5 minutes with a magnetic stirrer. The PTFE vessel is then transferred to an autoclave and then heated without stirring at 125° C. for 5 days. After cooling and filtration, the crystalline solid obtained is washed with methanol (Acros Organics, 99.99%), then with a hot solution (24 hours, 160° C.) of DMF (Aldrich, 99.8%) and is impregnated (48 hours) in dichloromethane (ACROS ORGANICS, 99.99%). After stove drying (air) at a temperature of 120° C. for 12 hours, a material in the form of powder constituted by crystals of CAU-1 is obtained.

Said crystallized hybrid solid CAU-1 is analysed by X-ray diffraction, by Fourier transform infrared spectroscopy and by proton nuclear magnetic resonance ($^1$H NMR).

X-ray diffraction analysis reveals that said solid thus obtained is identified as being constituted by solid CAU-1: the diffraction pattern obtained on said solid is identical to that presented in *Angew. Chem. Int. Ed,* 2009, Vol. 48, No. 28, 5163-5166. Analysis by FTIR reveals the presence of the amino function —$NH_2$ in the solid CAU-1. IR (KBr tablet), ν ($cm^{-1}$): 3454, 3386, 2935, 1669, 1574, 1432, 1393, 1260, 1066, 788, 607, 547. The bands at 3454 and 3386 $cm^{-1}$ are attributed to the amine function.

$^1$H NMR analysis is carried out on a sample of the solid CAU-1, after digestion and complete dissolution of the sample in a deuterated mixture $DCl/D_2O/DMSO$-$d_6$ according to the procedure described in the literature (Z. Q. Wang, S. M. Cohen, *Journal of the American Society,* 2007, 129, 12363-12369): 10 mg of hybrid solid CAU-1 is digested and dissolved in 1.5 mL of deuterated DMSO and 0.2 mL of a dilute solution of DCl (prepared from a solution containing 0.23 mL of $DCVD_2O$ at 35% and 1 mL of deuterated DMSO).

Combined with analysis by FTIR, $^1$H NMR analysis also reveals the presence of the amino group —$NH_2$ in the solid CAU-1. $^1$H NMR, 250 MHz, rt, δ (ppm/($DCl/D_2O/DMSO$-d6)): 6.88 (d, 1H, J=8 Hz); 7.03 (s, 1H); 7.6 (d, 1H, J=8 Hz).

Example 3.2

Preparation of a Functionalized Solid Bearing a Phenyl Function on the Triazole Ring, Using Phenylacetylene as Reagent with Alkene Terminal Function 80 mg (0.30 mmol equivalent —$NH_2$) of solid CAU-1 obtained at the end of the procedure described in Example 3.1 is dried for 12 hours at 85° C. under vacuum and is then placed in a pill machine (capacity 8 mL) with 3 mL (37 mmol, 123 eq) of THF, 0.74 mL (6.32 mmol, 21 eq) of tBuONO (Aldrich) and 0.65 mL (5 mmol, 17 eq) of TMS-$N_3$ (Aldrich).

After reaction overnight at ambient temperature and with stirring, 1.1 mL of phenylacetylene (10.1 mmol, 34 eq, Aldrich, 98%) and 54 mg of $Cu^I(CH_3CN)_4PF_6$ (0.29 mmol, 1 eq, Aldrich) in solution in 1 mL of THF (12.3 mmol, 41 eq) are added and the mixture is stirred for a further 12 h at ambient temperature. After filtration, the solid is washed 3 times with THF (×8 ml) and then 3 times with $CH_2Cl_2$ (×8 ml). The solid is finally dried under vacuum at ambient temperature overnight.

The CAU-1-functionalized solid obtained was analysed by X-ray diffraction. The diffraction pattern obtained on the CAU-1-functionalized solid shows that said solid has a crystalline structure identical to that of the solid CAU-1. XRD analysis carried out on the crystallized hybrid CAU-1-functionalized solid demonstrates that the post-modification functionalization treatment for replacing the amino function —$NH_2$ with the reactive group —$N_3CH$—C—$C_6H_5$ does not affect the structure and the crystallinity of the solid.

The functionalized solid CAU-1-CH—C—$C_6H_5$ is also analysed by FTIR and $^1$H NMR in the same way as described in Example 1.2. Comparison of the FTIR and $^1$H NMR spectra obtained for the solids CAU-1 and CAU-1-$N_3$—CH—C—$C_6H_5$ provides an estimate of 100% as the degree of modification of the amino functions —$NH_2$ to reactive groups —$N_3CH$—C—$C_6H_5$. The degree of modification of the nitride functions $N_3$ to reactive groups is shown in Table 1.

Example 3.3

Preparation of a Functionalized Solid Bearing a Tertiary Amine Function on the Triazole Ring, Using Diethylpropargyl Amine as Reagent with Alkyne Terminal Function This example is carried out following the same procedure as in Example 3.2. Diethylpropargyl amine $(CH_3CH_2)_2$—N—$CH_2$—CCH is used instead of phenylacetylene. The quantities of each of the reagents introduced are as follows:
Stage i):
CAU-1-$NH_2$: 80 mg (0.30 mmol equivalent —$NH_2$); THF: 3 mL (37 mmol, 123 eq); tBuONO: 0.74 mL (6.32 mmol, 21 eq); TMS-$N_3$: 0.65 mL (5 mmol, 17 eq).
Stage iii):
diethylpropargyl amine: 1.38 mL (9.6 mmol, 32 eq); $Cu^I(CH_3CN)_4PF_6$: 54 mg (0.29 mmol, 1 eq); THF: 1 ml (12.3 mmol, 41 eq).

The CAU-1-functionalized solid obtained was analysed by X-ray diffraction. The diffraction pattern obtained on the CAU-1-functionalized solid shows that said solid has a crystalline structure identical to that of the solid CAU-1. XRD analysis carried out on the crystallized hybrid CAU-1-functionalized solid demonstrates that the post-modification functionalization treatment for replacing the amino function —$NH_2$ with the reactive group —$N_3CH$—C—$CH_2$—N—$(CH_2$—$CH_3)_2$ does not affect the structure and the crystallinity of the solid.

The functionalized solid CAU-1-$N_3CH$—C—$CH_2$—N—$(CH_2CH_3)_2$ is also analysed by FTIR and $^1$H NMR in the same way as described in Example 1.2. Comparison of the FTIR and $^1$H NMR spectra obtained for the solids CAU-1 and CAU-1-$N_3CH$—C—$CH_2$—N—$(CH_2$—$CH_3)_2$ provides an estimate of 100% as the degree of modification of the amino functions —$NH_2$ to reactive groups —$N_3CH$—C—$CH_2$—N—$(CH_2$—$CH_3)_2$. The degree of modification of the nitride functions $N_3$ to reactive groups is shown in Table 1.

Example 3.4

Preparation of a Functionalized Solid Bearing a Function Constituted by a Heterocycle $C_5H_4N$ on the Triazole Ring Using the Reagent 2-Ethynylpyridine as Reagent with Alkene Terminal Function This example is carried out following the same procedure as in Example 3.2. 2-Ethynylpyridine $(C_5H_4N)$CCH is used instead of phenylacetylene.

The quantities of each of the reagents introduced are as follows:
Stage i):
CAU-1-$NH_2$; 80 mg (0.30 mmol equivalent —$NH_2$); THF: 3 mL (37 mmol, 123 eq); tBuONO: 0.74 mL (6.32 mmol, 21 eq); TMS-$N_3$: 0.65 mL (5 mmol, 17 eq).

Stage iii):
2-ethynylpyridine: 0.96 ml (9.45 mmol, 31.5 eq); Cu$^I$(CH$_3$CN)$_4$PF$_6$: 48 mg (0.26 mmol, 0.9 eq); THF: 1 ml (12.3 mmol, 41 eq).

The solid obtained was analysed by X-ray diffraction. The diffraction pattern obtained on the CAU-1-functionalized solid shows that said solid has a crystalline structure identical to that of the solid CAU-1. XRD analysis carried out on the crystallized hybrid CAU-1-functionalized solid demonstrates that the post-modification functionalization treatment for replacing the amino function —NH$_2$ with the reactive group —N$_3$CH—C—C$_5$H$_4$N does not affect the structure and the crystallinity of the solid.

The functionalized solid CAU-1-N$_3$CH—C—C$_5$H$_4$N is also analysed by FTIR and $^1$H NMR in the same way as described in Example 1.2. Comparison of the FTIR and $^1$H NMR spectra obtained for the solids CAU-1-NH$_2$ and CAU-1-N$_3$CH—C—C$_5$H$_4$N finds 100% modification of the amino functions —NH$_2$ to reactive groups —N$_3$CH—C—C$_5$H$_4$N. The degree of modification of the nitride functions N$_3$ to reactive groups —N$_3$CH—C—C$_5$H$_4$N is shown in Table 1.

Example 4

Preparation of Functionalized Solids from the Crystallized Hybrid Solid IHM-2

Example 4.1

Preparation of the Crystallized Hybrid Solid IHM-2

4.82 mL (3.3 mmol) of a solution of indium nitrate (Alfa Aesar, 99.99%) in dimethylformamide (DMF, Aldrich, 99.8%) at a concentration of 0.68 mol/L is placed in a Pyrex vessel of 100 mL capacity, and 10.06 mL (3.3 mmol) of a solution of 2-amino-1,4-benzene dicarboxylic acid (Alfa Aesar, 99%) in DMF at a concentration of 0.33 mol/L is added. The mixture is stirred for 5 minutes with a magnetic stirrer. After homogenization, 4.83 mL (6.7 mmol) of a solution of 1,4-diazabicyclo[2.2.2]octane (DABCO, Aldrich, 98%) in DMF at a concentration of 1.38 mol/L is added. The solution is stirred for 120 minutes at ambient temperature. After cooling and filtration, the crystalline solid obtained is washed (24 hours) with a hot solution (160° C.) of DMF and then is impregnated with dichloromethane (48 hours). After drying in air at a temperature of 120° C. for 12 hours, a material in the form of powder constituted by crystals of IHM-2 is obtained.

Said crystallized hybrid solid IHM-2 is analysed by X-ray diffraction, by Fourier transform infrared spectroscopy and by proton nuclear magnetic resonance ($^1$H NMR).

X-ray diffraction analysis reveals that said solid thus obtained is identified as being constituted by solid IHM-2: the diffraction pattern obtained on the solid IHM-2 is that shown in FIG. 1.

Analysis by FTIR reveals the presence of the amino function —NH$_2$ in the solid IHM-2.
IR (KBr tablet), ν (cm$^{-1}$): 3450, 3379, 2975, 1660, 1623, 1556, 1423, 1381, 1256, 1044, 829, 790, 770, 699, 579, 522. The bands at 3450 and 3379 cm$^{-1}$ are attributed to the amine function.

$^1$H NMR analysis is carried out on a sample of the solid IHM-2, after digestion and complete dissolution of the sample in a deuterated mixture DCl/D$_2$O/DMSO-d$_6$ according to the procedure described in the literature (Z. Q. Wang, S. M. Cohen, *Journal of the American Society*, 2007, 129, 12368-12369): 10 mg of hybrid solid IHM-2 is digested and dissolved in 1.5 mL of deuterated DMSO and 0.2 mL of a dilute solution of DCl (prepared from a solution containing 0.23 mL of DCl/D$_2$O at 35% and 1 mL of deuterated DMSO).

$^1$H NMR analysis also reveals the presence of the amino group —NH$_2$ in the solid IHM-2. $^1$H NMR, 250 MHz, rt, δ (ppm/(DCl/D$_2$O/DMSO-d$_6$)): 7.15 (d, 1H, J=8.3 Hz); 7.44 (s, 1H); 7.80 (d, 1H, J=8.3 Hz).

Example 4.2

Preparation of a Functionalized Solid Bearing a Phenyl Function on the Triazole Ring, Using Phenylacetylene as Reagent with Alkyne Terminal Function 80 mg (0.26 mmol equivalent —NH$_2$) of solid IHM-2 obtained at the end of the procedure described in Example 4.1 is dried for 12 hours at 85° C. under vacuum and is then placed in a pill machine (capacity 8 mL) with 3 mL (37 mmol, 142.3 eq) of THF, 1.48 mL (12.48 mmol, 48 eq) of tBuONO (Aldrich) and 1.3 mL (9.88 mmol, 38 eq) of TMS-N$_3$ (Aldrich).

After reaction overnight at ambient temperature and with stirring, 0.96 mL of phenylacetylene (8.8 mmol, 33.8 eq, Aldrich. 98%) and 48 mg of Cu$^I$(CH$_3$CN)$_4$PF$_6$ (0.26 mmol, 1 eq, Aldrich) in solution in 1 mL of THF (12.3 mmol, 47 eq) are added and the mixture is stirred for a further 12 h at ambient temperature. After filtration, the solid is washed 3 times with THF (×8 ml) and then 3 times with CH$_2$Cl$_2$ (×8 ml). The solid is finally dried under vacuum at ambient temperature overnight.

The IHM-2-functionalized solid obtained was analysed by X-ray diffraction. The diffraction pattern obtained on the IHM-2-functionalized solid shows that said solid has a crystalline structure identical to that of the solid IHM-2. XRD analysis carried out on the crystallized hybrid IHM-2-functionalized solid demonstrates that the post-modification functionalization treatment for replacing the amino function —NH$_2$ with the reactive group —N$_3$CH—C—C$_6$H$_5$ does not affect the structure and the crystallinity of the solid.

The functionalized solid IHM-2-N$_3$—CH—C—C$_6$H$_5$ is also analysed by FTIR and $^1$H NMR in the same way as described in Example 1.2. Comparison of the FTIR and $^1$H NMR spectra obtained for the solids IHM-2 and IHM-2-N$_3$—CH—C—C$_6$H$_5$ provides an estimate of 100% as the degree of modification of the amino functions —NH$_2$ to reactive groups —N$_3$CH—C—C$_6$H$_5$. The degree of modification of the nitride functions N$_3$ to reactive groups is shown in Table 1.

Example 4.3

Preparation of a Functionalized Solid Bearing a Tertiary Amine Function on the Triazole Ring, Using Diethylpropargyl Amine as Reagent with Alkene Terminal Function This example is carried out following the same procedure as in Example 4.2. Diethylpropargyl amine (CH$_3$CH$_2$)$_2$—N—CH$_2$—CCH is used instead of phenylacetylene. The quantities of each of the reagents introduced are as follows:
Stage i):
IHM-2: 80 mg (0.26 mmol equivalent —NH$_2$); THF: 3 mL (37 mmol, 142.3 eq); tBuONO: 1.48 mL (12.48 mmol, 48 eq); TMS-N$_3$: 1.3 mL (9.88 mmol, 38 eq).
Stage ii);
diethylpropargyl amine: 2.44 mL (17 mmol, 65.4 eq); Cu$^I$(CH$_3$CN)$_4$PF$_6$: 96 mg (0.52 mmol, 2 eq); THF: 1 ml (12.3 mmol, 47 eq).

The IHM-2-functionalized solid obtained was analysed by X-ray diffraction. The diffraction pattern obtained on the IHM-2-functionalized solid shows that said solid has a crystalline structure identical to that of the solid IHM-2. XRD analysis carried out on the crystallized hybrid IHM-2-functionalized solid demonstrates that the post-modification functionalization treatment for replacing the amino function —NH$_2$ with the reactive group —N$_3$CH—C—CH$_2$—N—(CH$_2$—CH$_3$)$_2$ does not affect the structure and the crystallinity of the solid.

The functionalized solid IHM-2-N$_3$CH—C—CH$_2$—N—(CH$_2$CH$_3$)$_2$ is also analysed by FTIR and $^1$H NMR in the same way as described in Example 1.2. Comparison of the FTIR and $^1$H NMR spectra obtained for the solids IHM-2 and IHM-2-N$_3$CH—C—CH$_2$—N—(CH$_2$—CH$_3$)$_2$ provides an estimate of 100% as the degree of modification of the amino functions —NH$_2$ to reactive groups —N$_3$CH—C—CH$_2$—N—(CH$_2$CH$_3$)$_2$. The degree of modification of the nitride functions N$_3$ to reactive groups is shown in Table 1.

Example 4.4

Preparation of a Functionalized Solid Bearing a Function Constituted by a Heterocycle C$_5$H$_4$N on the Triazole Ring Using the Reagent 2-Ethynylpyridine as Reagent with Alkyne Terminal Function This example is carried out following the same procedure as in Example 4.2. 2-Ethynylpyridine (C$_6$H$_4$N)CCH is used instead of phenylacetylene.

The quantities of each of the reagents introduced are as follows:

Stage i):

IHM-2: 80 mg (0.26 mmol equivalent —NH$_2$); THF: 3 mL (37 mmol, 142.3 eq); tBuONO: 1.48 mL (12.48 mmol, 48 eq); TMS-N$_3$: 1.3 mL (9.88 mmol, 38 eq).

Stage iii):

2-ethynylpyridine: 0.84 ml (8.3 mmol, 32 eq); Cu$^I$(CH$_3$CN)$_4$PF$_6$: 48 mg (0.26 mmol, 1 eq); THF: 1 ml (12.3 mmol, 47 eq).

The IHM-2-functionalized solid obtained was analysed by X-ray diffraction. The diffraction pattern obtained on the IHM-2-functionalized solid shows that said solid has a crystalline structure identical to that of the solid IHM-2. XRD analysis carried out on the crystallized hybrid IHM-2-functionalized solid demonstrates that the post-modification functionalization treatment for replacing the amino function —NH$_2$ with the reactive group —N$_3$CH—C—C$_5$H$_4$N does not affect the structure and the crystallinity of the solid.

The functionalized solid IHM-2-N$_3$CH—C—C$_5$H$_4$N is also analysed by FTIR and $^1$H NMR in the same way as described in Example 1.2. Comparison of the FTIR and $^1$H NMR spectra obtained for the solids IHM-2 and IHM-2-N$_3$CH—C—C$_5$H$_4$N provides an estimate of 100% as the degree of modification of the amino functions —NH$_2$ to reactive groups —N$_3$CH—C—C$_6$H$_4$N. The degree of modification of the nitride functions N$_3$ to reactive groups —N$_3$CH—C—C$_6$H$_4$N is shown in Table 1.

TABLE 1 degree of modification of the nitride functions N$_3$ present in the intermediate solid to reactive groups present in the functionalized solid

| MOF-NH$_2$ starting solid | Phenyl-acetylene graft C$_6$H$_5$CCH | Diethylpropargyl amine graft (CH$_3$CH$_2$)$_2$N—CH$_2$—CCH | 2-Ethynylpyridine graft (C$_5$H$_4$N)CCH |
|---|---|---|---|
| DMOF-1-NH$_2$ | 100 | 90 | 80 |
| MIL-53-Al—NH$_2$ | 92 | — | 64 |
| CAU-1 | 100 | 81 | 50 |
| IHM-2 | 77 | 73 | 20 |

It will be recalled that the degree of modification of the nitride functions N$_3$ to reactive groups —N$_3$—CH—CR, shown in Table 1, is calculated by quantifying the decrease in relative area of the signals from the aromatic protons of the intermediate solid relative to those from the functionalized solid.

The results shown in Table 1 demonstrate that the process according to the invention can lead either to complete or at least very high substitution (degree of substitution=77, 80, 90, 92%) of the nitride functions —N$_3$ with reactive groups or to partial substitution of the nitride functions —N$_3$ with reactive groups. Control of the degree of modification of the nitride functions N$_3$ to reactive groups constitutes an essential advantage of the process of the invention.

The invention claimed is:

1. Process for the preparation of a functionalized hybrid solid with an organic-inorganic matrix, crystallized, bearing at least one reactive group based on a triazole ring, from a crystallized hybrid solid with an organic-inorganic matrix, MOF—NH$_2$, containing an inorganic network of metallic sites joined together at least by organic ligands comprising at least one aromatic ring, at least two carboxylate functions CO$_2^-$ and at least one amine function —NH$_2$, said process comprising at least the following successive stages:

i/ introduction, in a polar solvent S1, of said crystallized hybrid solid MOF—NH$_2$, at least one organic compound Q containing a nitride function N$_3$ and at least one intermediate reagent R containing a nitrite function NO$_2$ in proportions such that the reaction mixture has the following molar composition, based on one molar equivalent of the function —NH$_2$ present in the solid MOF—NH$_2$:

1MOF—NH$_2$:1-150R:1-150Q:100-400S1 ii/ reaction of said reaction mixture at a temperature between 0 and 100° C. for a time between 1 and 24 hours, iii/ introduction, in the reaction mixture, of at least one reagent A comprising at least one alkyne or activated cyanide COCN terminal function, at least one copper-based catalyst C and at least one polar solvent S2 in proportions such that the reaction mixture has the following composition, based on one molar equivalent of the function —NH$_2$ present initially in the solid MOF—NH$_2$:

1MOF—NH$_2$:0.1-10C:1-150R:1-150Q:1-150A:100-600(S1+S2)

iv/ reaction of said reaction mixture at a temperature between 0 and 100° C. for a time between 1 and 48 hours, v/ filtration and then washing of said crystallized functionalized hybrid solid, vi/ drying of said crystallized functionalized hybrid solid.

2. Process for the preparation of a functionalized solid according to claim 1, characterized in that said reactive group based on said triazole ring has the empirical formula —$N_3$—CH—CR, where R is a function selected from the benzyl, phenyl, aromatic heterocycle and amine functions.

3. Process for the preparation of a functionalized solid according to claim 1, characterized in that said functionalized solid has a crystalline structure identical to that of the solid MOF—$NH_2$ from which it is derived.

4. Preparation process according to claim 1, characterized in that said organic ligands present in said solid MOF—$NH_2$ are formed by the entity 2-aminoterephthalate-$O_2C$—$C_6H_3$—$NH_2$—$CO_2$ (ligand $NH_2$-bdc).

5. Preparation process according to claim 4, characterized in that said solid MOF—$NH_2$, used for implementing said stage i), is selected from the solids Fe(OH)($NH_2$-bdc), $Fe_3O$(solv)$_3$Cl($NH_2$-bdc)$_3$, $Zn_3$($NH_2$-bdc)$_3$($H_2O$)$_2$, $Zn_2$($NH_2$-bdc)$_2$(dabco), Al(OH)($NH_2$-bdc), $Al_4$(OH)$_2$(OCH$_3$)$_4$($NH_2$-bdc)$_3$ $Zn_4$O($NH_2$-bdc)$_3$ and In(OH)($NH_2$-bdc).

6. Preparation process according to claim 1, characterized in that said crystallized hybrid solid MOF—$NH_2$ is previously dried before being introduced into said polar solvent S1.

7. Preparation process according to claim 1, characterized in that said organic compound Q, used for implementing said stage i), is selected from trimethylsilyl nitride (($CH_3$)$_3$Si$N_3$), triflyl nitride (Tf$N_3$, where Tf=$CF_3SO_2$), p-tosyl nitride ($C_6H_4$($CH_3$)$SO_2N_3$) and sodium nitride (Na$N_3$).

8. Preparation process according to claim 1, characterized in that said intermediate reagent R containing a nitrite function $NO_2$, used for implementing said stage i), is tert-butyl-nitrite (tBuONO).

9. Preparation process according to claim 1, characterized in that reagent A, used for implementing said stage iii), comprises simultaneously at least one alkyne or activated cyanide COCN terminal function and a function R selected from the benzyl, phenyl, aromatic heterocycle and amine functions.

10. Preparation process according to claim 9, characterized in that said reagent A is selected from phenylacetylene, 2-ethynylpyridine ($C_6H_5$CCH), diethylpropargyl amine (($CH_3CH_2$)$_2$N—$CH_2$CCH) and benzoyl cyanide ($C_6H_5$COCN).

11. Preparation process according to claim 1, characterized in that said stage iii) is carried out in the presence of several reagents A each having a function R different from one other.

12. Preparation process according to claim 1, characterized in that said copper-based catalyst C, used for implementing said stage iii), is selected from the copper compounds having an oxidation number of the copper equal to 1 (Cu(I)) or having an oxidation number of the copper equal to 2 (Cu(II)) in the presence of a reducing agent.

13. Preparation process according to claim 12, characterized in that said catalyst C is selected from the copper compounds having an oxidation number of the copper equal to 1 (Cu(I)).

14. Preparation process according to claim 1, characterized in that said polar solvents S1 and S2 are selected with the same chemical composition or with different chemical composition.

15. Preparation process according to claim 1, characterized in that said reaction stage iv) is carried out at a temperature between 0 and 60° C.

* * * * *